(12) United States Patent
Samsoondar

(10) Patent No.: US 7,740,804 B2
(45) Date of Patent: Jun. 22, 2010

(54) SPECTROSCOPIC SAMPLE HOLDER

(75) Inventor: James Samsoondar, Markham (CA)

(73) Assignee: Chromedx Inc., Markham, Ontario (CA)

( * ) Notice: Subject to any disclaimer, the term of this patent is extended or adjusted under 35 U.S.C. 154(b) by 0 days.

(21) Appl. No.: 12/016,315

(22) Filed: Jan. 18, 2008

(65) Prior Publication Data
US 2008/0180658 A1 Jul. 31, 2008

Related U.S. Application Data

(63) Continuation of application No. 11/103,619, filed on Apr. 12, 2005, now abandoned.

(51) Int. Cl.
*G01N 21/11* (2006.01)
(52) U.S. Cl. ...................... 422/68.1; 356/246
(58) Field of Classification Search ........................ None
See application file for complete search history.

(56) References Cited

U.S. PATENT DOCUMENTS

| | | | |
|---|---|---|---|
| 3,874,850 A | | 4/1975 | Sorenson et al. |
| 4,013,417 A | * | 3/1977 | Raffaele ...................... 422/67 |
| 4,088,448 A | | 5/1978 | Lilja et al. |
| 4,409,106 A | | 10/1983 | Furuta et al. |
| 4,613,422 A | | 9/1986 | Lauks |
| 4,668,399 A | | 5/1987 | Duggins |
| 4,695,274 A | | 9/1987 | Fox |
| 4,756,884 A | * | 7/1988 | Hillman et al. ............... 422/73 |
| 4,849,340 A | | 7/1989 | Oberhardt |
| 4,900,310 A | | 2/1990 | Ogle, II |
| 5,096,669 A | | 3/1992 | Lauks et al. |
| 5,112,455 A | | 5/1992 | Cozzette et al. |
| 5,430,542 A | | 7/1995 | Shepherd |
| 5,638,828 A | | 6/1997 | Lauks et al. |
| 5,725,574 A | | 3/1998 | Nguyen |

(Continued)

FOREIGN PATENT DOCUMENTS

JP 60-011166 1/1985

(Continued)

OTHER PUBLICATIONS

Office Action issued in connection with co-pending U.S. Appl. No. 11/103,619, filed Apr. 12, 2005, mailed on Jan. 5, 2009 (retrievable from Pair).

(Continued)

*Primary Examiner*—Jill Warden
*Assistant Examiner*—Timothy G Kingan
(74) *Attorney, Agent, or Firm*—Ian C. McMillan; Bereskin & Parr LLP/S.E.N.C.R.L., s.r.l.

(57) ABSTRACT

Some embodiments of the present invention provide a sample holder that is suitable for collection and spectroscopic measurement of a blood sample. In some embodiments, the sample holder is provided with an optical chamber that is specifically designed to spread blood into a thin film, thereby reducing the average attenuation of electromagnetic radiation (EMR) due to scattering of EMR by the red blood cells in a blood sample, without having to hemolyze the red blood cells using sound waves or reagents. The inlet of some embodiments of the sample holder is a piece of capillary tube, and in other embodiments, the inlet is configured to engage a syringe. In some embodiments, the inlet of the sample holder can accommodate adaptors with different configurations, thereby allowing the sample holder to receive blood from any source, for example a pin prick or a syringe.

8 Claims, 13 Drawing Sheets

U.S. PATENT DOCUMENTS

| | | | |
|---|---|---|---|
| 5,725,774 A | 3/1998 | Neyer | |
| 5,957,579 A * | 9/1999 | Kopf-Sill et al. | 366/340 |
| 5,976,433 A | 11/1999 | Komatsu et al. | |
| 6,066,243 A | 5/2000 | Anderson et al. | |
| 6,130,098 A * | 10/2000 | Handique et al. | 436/180 |
| 6,143,247 A | 11/2000 | Sheppard et al. | |
| 6,155,991 A | 12/2000 | Beat et al. | |
| 6,262,798 B1 | 7/2001 | Shepherd et al. | |
| 6,348,156 B1 | 2/2002 | Vishnoi et al. | |
| 6,581,441 B1 * | 6/2003 | Paul | 73/61.52 |
| 6,596,438 B2 | 7/2003 | Cabuz et al. | |
| 6,695,147 B1 | 2/2004 | Yager et al. | |
| 6,787,368 B1 | 9/2004 | Wong et al. | |
| 6,878,271 B2 | 4/2005 | Gilbert | |
| 6,962,823 B2 | 11/2005 | Empedocies et al. | |
| 6,966,880 B2 | 11/2005 | Boecker et al. | |
| 7,018,838 B2 | 3/2006 | Murphy et al. | |
| 7,094,345 B2 | 8/2006 | Gilbert et al. | |
| 7,258,774 B2 | 8/2007 | Chou et al. | |
| 7,314,718 B1 | 1/2008 | Dasgupta et al. | |
| 2002/0025576 A1 * | 2/2002 | Northrup et al. | 435/288.5 |
| 2002/0045272 A1 | 4/2002 | McDevitt et al. | |
| 2002/0091057 A1 | 7/2002 | Westberg et al. | |
| 2002/0100714 A1 * | 8/2002 | Staats | 210/85 |
| 2002/0106786 A1 * | 8/2002 | Carvalho et al. | 435/287.3 |
| 2002/0142471 A1 | 10/2002 | Handique et al. | |
| 2002/0143437 A1 | 10/2002 | Handique et al. | |
| 2002/0164824 A1 | 11/2002 | Xiao et al. | |
| 2002/0177135 A1 | 11/2002 | Doung et al. | |
| 2002/0187072 A1 | 12/2002 | Karp | |
| 2002/0187074 A1 * | 12/2002 | O'Connor et al. | 422/82.05 |
| 2002/0197167 A1 | 12/2002 | Korneisen | |
| 2003/0049862 A1 * | 3/2003 | He et al. | 436/180 |
| 2003/0123047 A1 | 7/2003 | Pettersen et al. | |
| 2003/0175990 A1 | 9/2003 | Hayenga et al. | |
| 2003/0209451 A1 | 11/2003 | Dineen et al. | |
| 2003/0215855 A1 | 11/2003 | Dubrow et al. | |
| 2004/0089616 A1 * | 5/2004 | Kellogg et al. | 210/749 |
| 2004/0176704 A1 | 9/2004 | Stevens et al. | |
| 2004/0176705 A1 | 9/2004 | Stevens et al. | |
| 2004/0189311 A1 * | 9/2004 | Glezer et al. | 324/444 |
| 2004/0224362 A1 | 11/2004 | Gjerde et al. | |
| 2004/0254419 A1 | 12/2004 | Wang et al. | |
| 2005/0026273 A1 | 2/2005 | Zarur et al. | |
| 2005/0130226 A1 * | 6/2005 | Ahn et al. | 435/7.1 |
| 2005/0130292 A1 * | 6/2005 | Ahn et al. | 435/287.1 |
| 2005/0152808 A1 | 7/2005 | Ganesan | |
| 2005/0153434 A1 | 7/2005 | Andersson et al. | |
| 2005/0233352 A1 | 10/2005 | Zoval | |
| 2006/0257941 A1 | 11/2006 | McDevitt et al. | |
| 2007/0052956 A1 * | 3/2007 | Blair | 356/246 |
| 2007/0150223 A1 | 6/2007 | Abraham-Fuchs et al. | |

OTHER PUBLICATIONS

Office Action issued in connection with co-pending U.S. Appl. No. 11/415,284, filed May 2, 2006, mailed on Jan. 23, 2009 (retrievable from Pair).

Office Action issued in connection with co-pending U.S. Appl. No. 11/466,588, filed Aug. 23, 2006, mailed on Feb. 20, 2009 (retrievable from Pair).

Office Action issued in connection with co-pending U.S. Appl. No. 11/432,616, filed May 12, 2006 (retrievable from Pair), mailed on Oct. 7, 2008.

Office Action issued in connection with co-pending U.S. Appl. No. 11/835,631, filed Aug. 8, 2007 (retrievable from Pair), mailed on Oct. 6, 2008.

Response filed in connection with co-pending U.S. Appl. No. 11/103,619, filed Apr. 12, 2005 (retrievable from Pair).

Office Action issued in connection with co-pending U.S. Appl. No. 11/108,912, filed Apr. 19, 2005 (retrievable from PAIR), mailed on Jul. 10, 2008.

Office Action issued in connection with co-pending U.S. Appl. No. 11/103,619, filed Apr. 12, 2005 (retrievable from PAIR), mailed on Jun. 25, 2008.

Office Action issued in connection with co-pending U.S. Appl. No. 11/415,284, filed May 2, 2006 (retrievable from PAIR), mailed on Aug. 20, 2008.

Co-pending U.S. Appl. No. 11/432,616, "Diagnostic Whole Blood and Plasma Apparatus", May 12, 2006. (Retrievable from PAIR).

Co-pending U.S. Appl. No. 11/466,588, "Hollow Needle Assembly", filed Aug. 23, 2006. (Retrievable from PAIR).

Co-pending U.S. Appl. No. 11/738,889, "Hollow Needle Assembly" (CIP), filed Apr. 23, 2007. (Retrievable from PAIR).

Co-pending U.S. Appl. No. 11/835,631, "Plasma Extraction Apparatus" (CIP), filed Aug. 8, 2007. (Retrievable from PAIR).

Co-pending U.S. Appl. No. 11/108,912, "Joint-Diagnostic Spectroscopic and Biosensor Cartridge", filed Apr. 19, 2005. (Retrievable from PAIR).

Co-pending U.S. Appl. No. 11/415,284, "Joint-Diagnostic Spectroscopic and Biosensor Meter" CIP, filed May 2, 2006. (Retrievable from PAIR).

Co-pending U.S. Appl. No. 11/103,619, "Blood Collection and Measurement Apparatus", filed Apr. 12, 2005. (Retrievable from PAIR).

Office Action issued in connection with co-pending U.S. Appl. No. 11/432,616, filed May 12, 2006 (retrievable from PAIR), mailed on Apr. 16, 2009.

Office Action issued in connection with co-pending U.S. Appl. No. 11/432,616 (retrievable from Pair), mailed on Sep. 17, 2009.

Office Action issued in connection with co-pending U.S. Appl. No. 11/432,616, mailed on Sep. 17, 2009.

Waters Medical Systems, "OXIMETRY", retrieved from http://www.watersmed.com/oximetry.html, dated Sep. 30, 2004.

Office Action issued in connection with co-pending U.S. Appl. No. 11/835,631, filed Aug. 8, 2007, mailed on Jun. 19, 2009.

Office Action issued in connection with co-pending U.S. Appl. No. 11/415,284, filed May 12, 2006, mailed on Aug. 5, 2008.

Office Action issued in connection with co-pending U.S. Appl. No. 11/103,619, filed Apr. 12, 2005, mailed on Jan. 5, 2009.

K.A. Erickson and P.Wilding, Clinical Chemistry 39(2): 283-287, 1993.

Restriction Requirement Office Action issued in connection with co-pending U.S. Appl. No. 11/466,588, filed Aug. 23, 2006, mailed on Feb. 20, 2009.

Office Action issued in connection with co-pending U.S. Appl. No. 11/415,284, filed May 2, 2006, mailed on Nov. 25, 2009.

Office Action issued in connection with co-pending U.S. Appl. No. 11/835,634, filed on Aug. 8, 2007, mailed on Mar. 25, 2010.

Advisory Action received on the co-pending U.S. Appl. No. 11/415,284, filed on May 2, 2006, mailed on Feb. 22, 2010.

Office Action received on the co-pending U.S. Appl. No. 11/415,284 filed on May 2, 2006, mailed on Apr. 13, 2010.

* cited by examiner

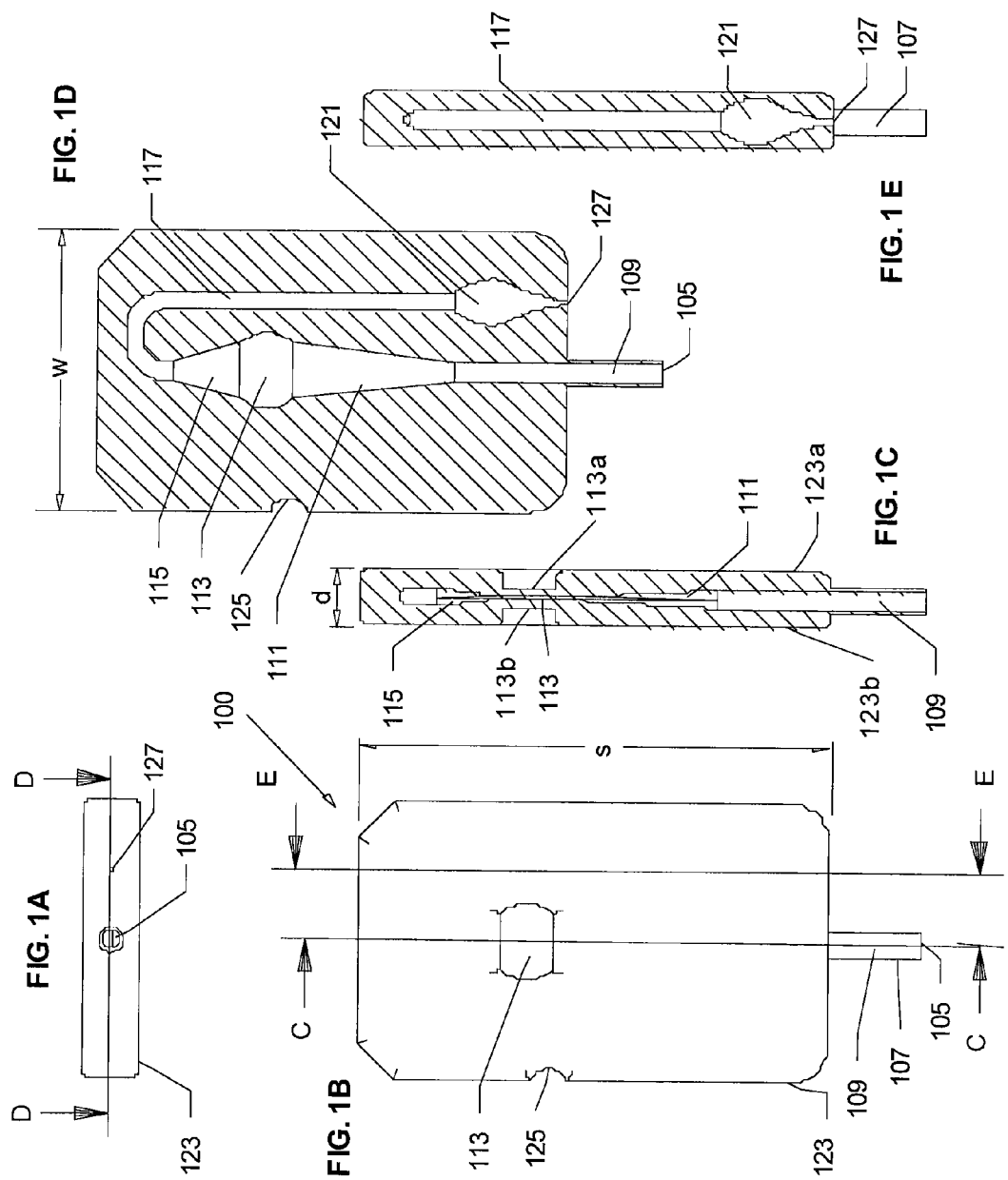

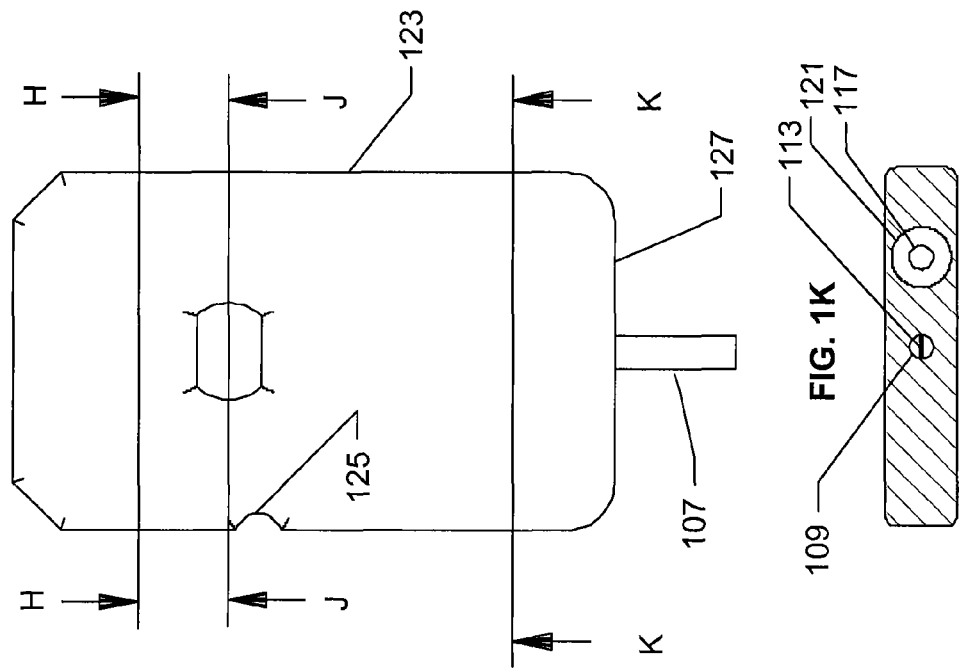
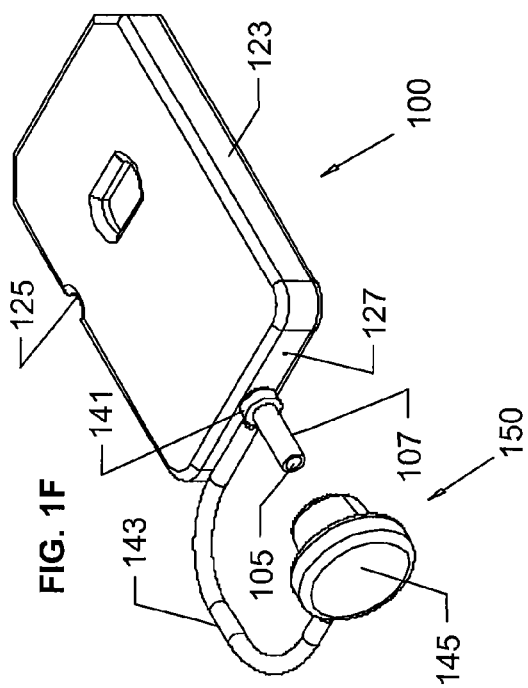
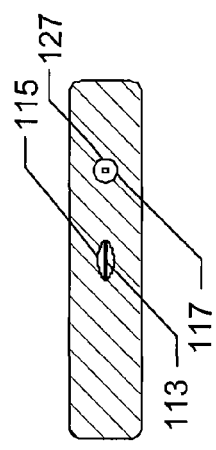
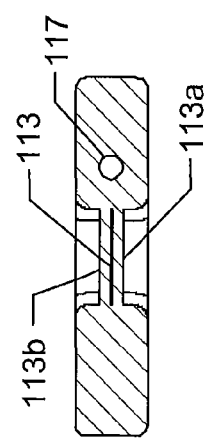

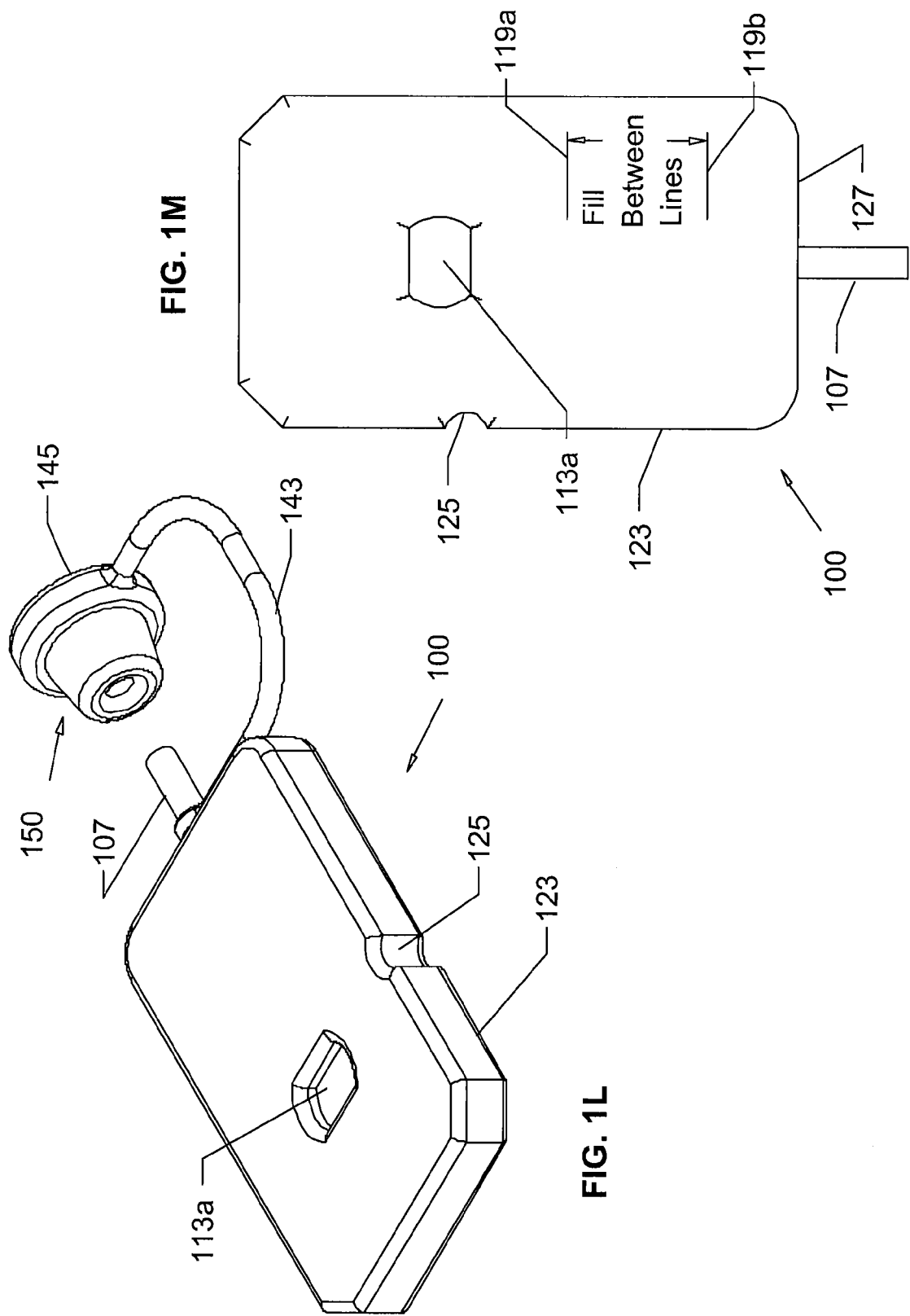

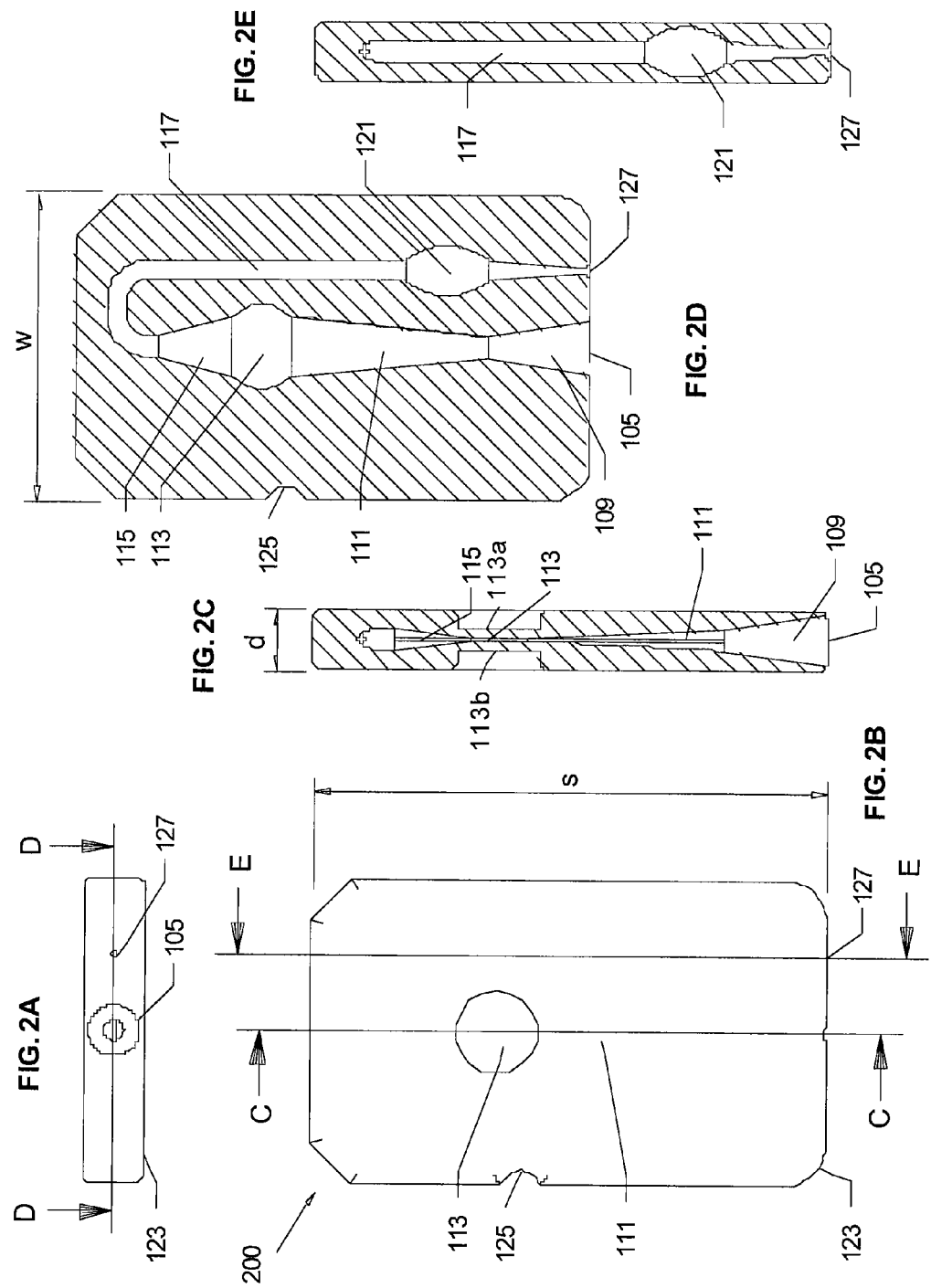

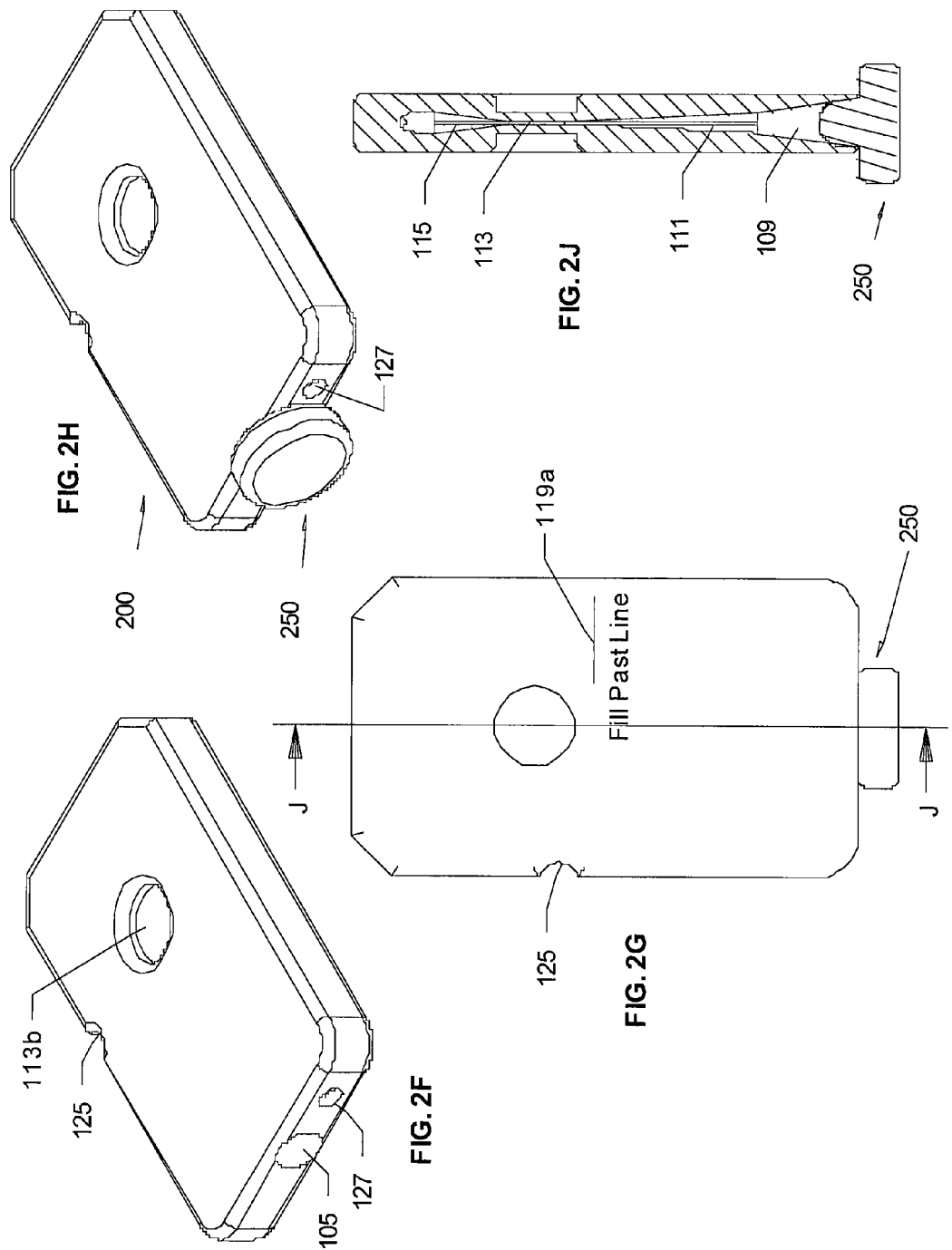

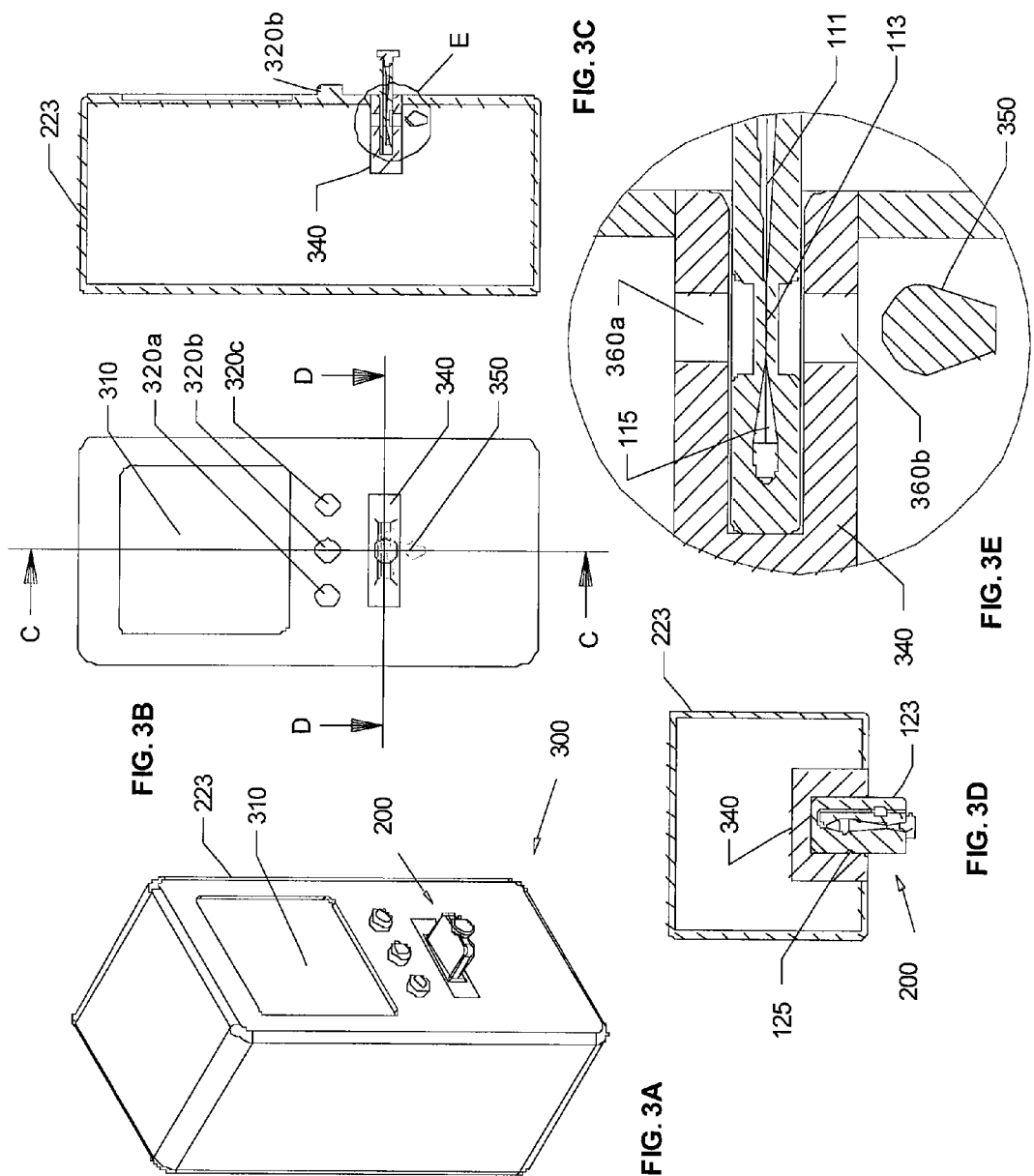

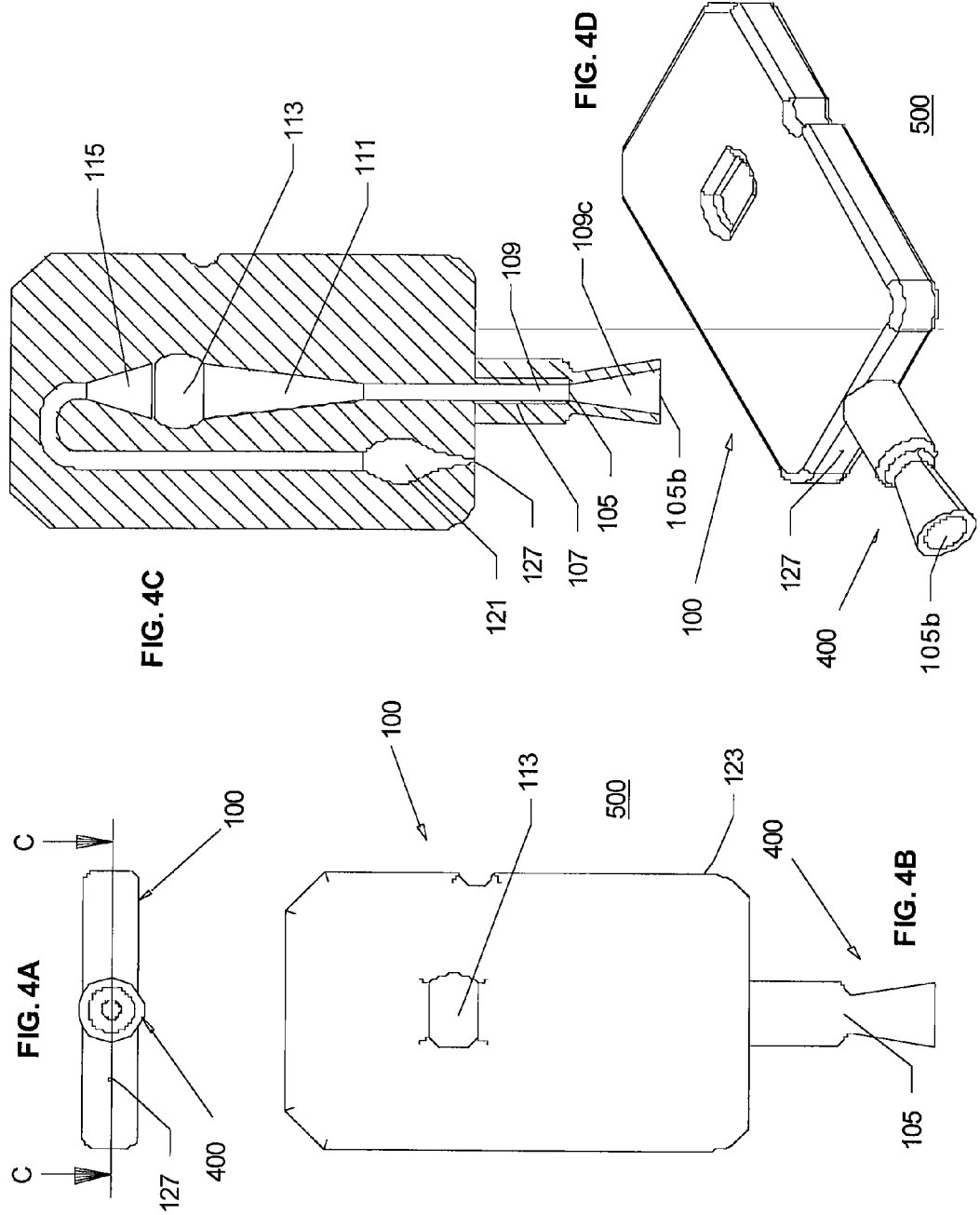

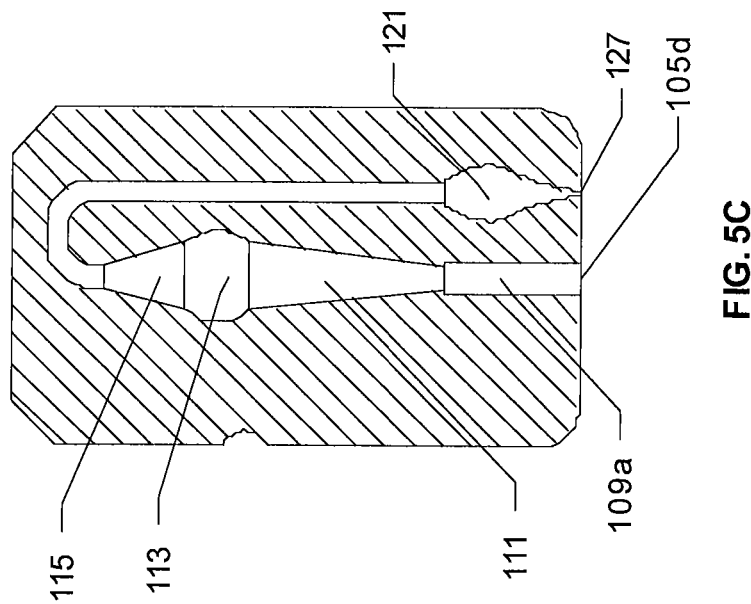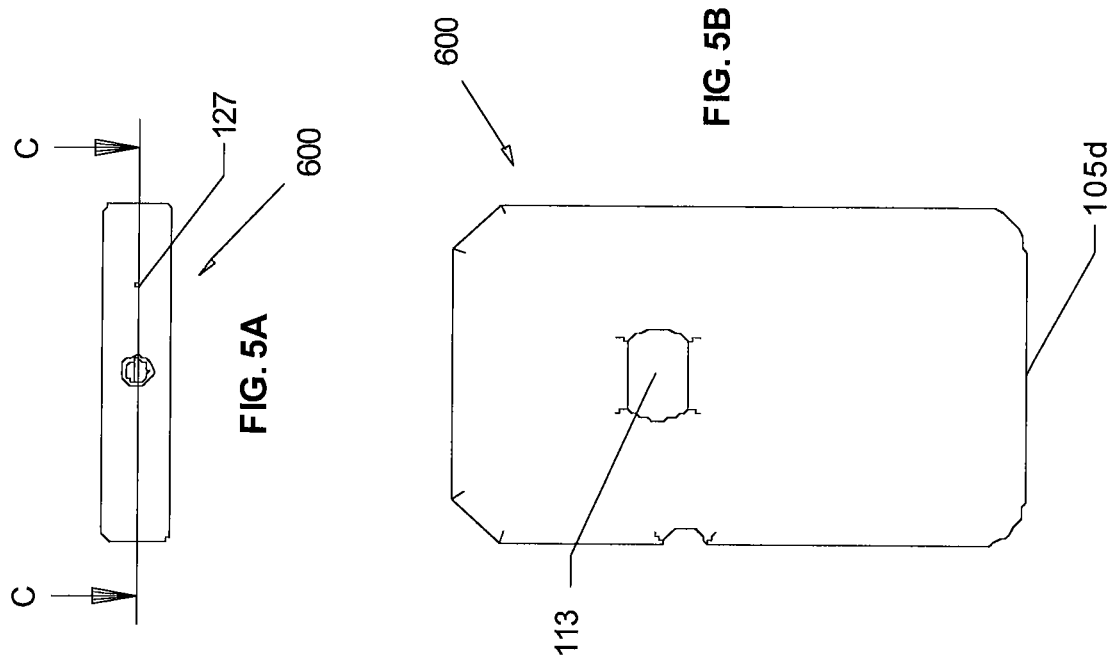

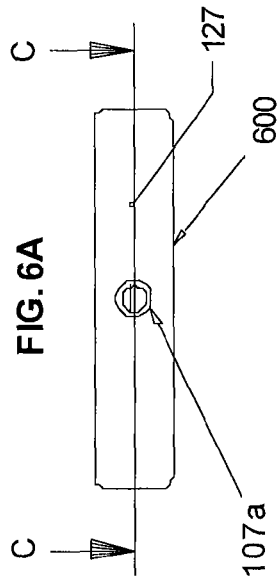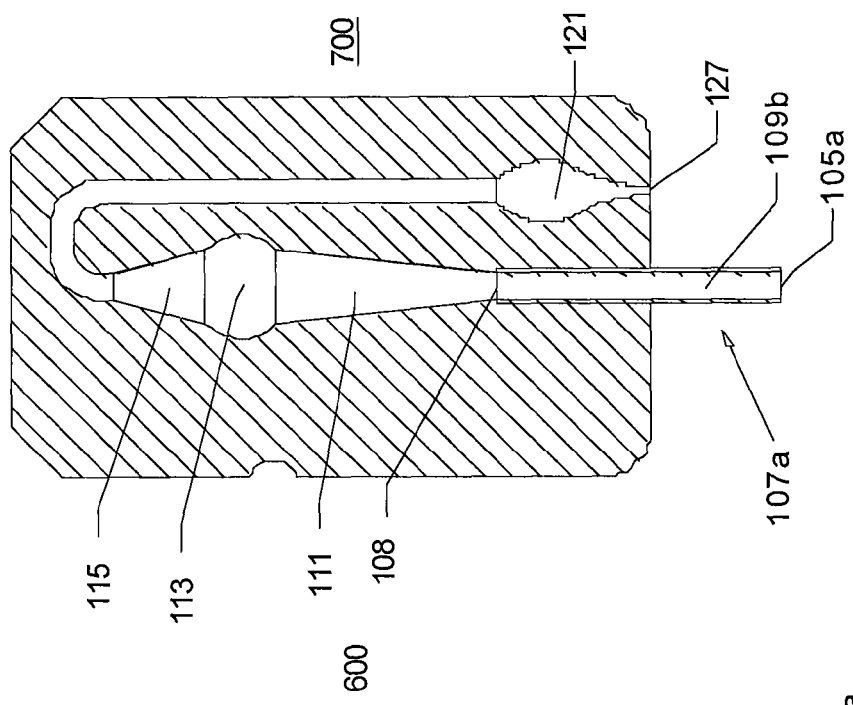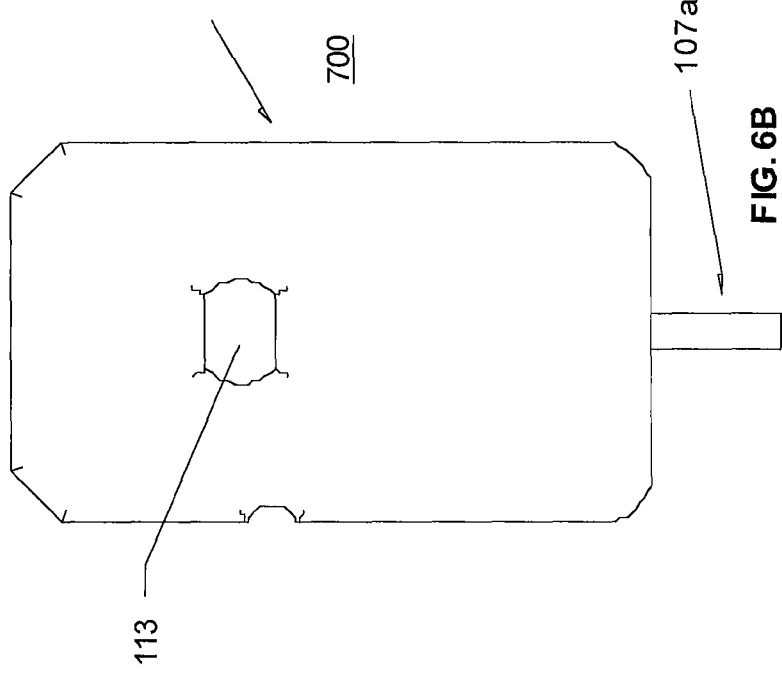

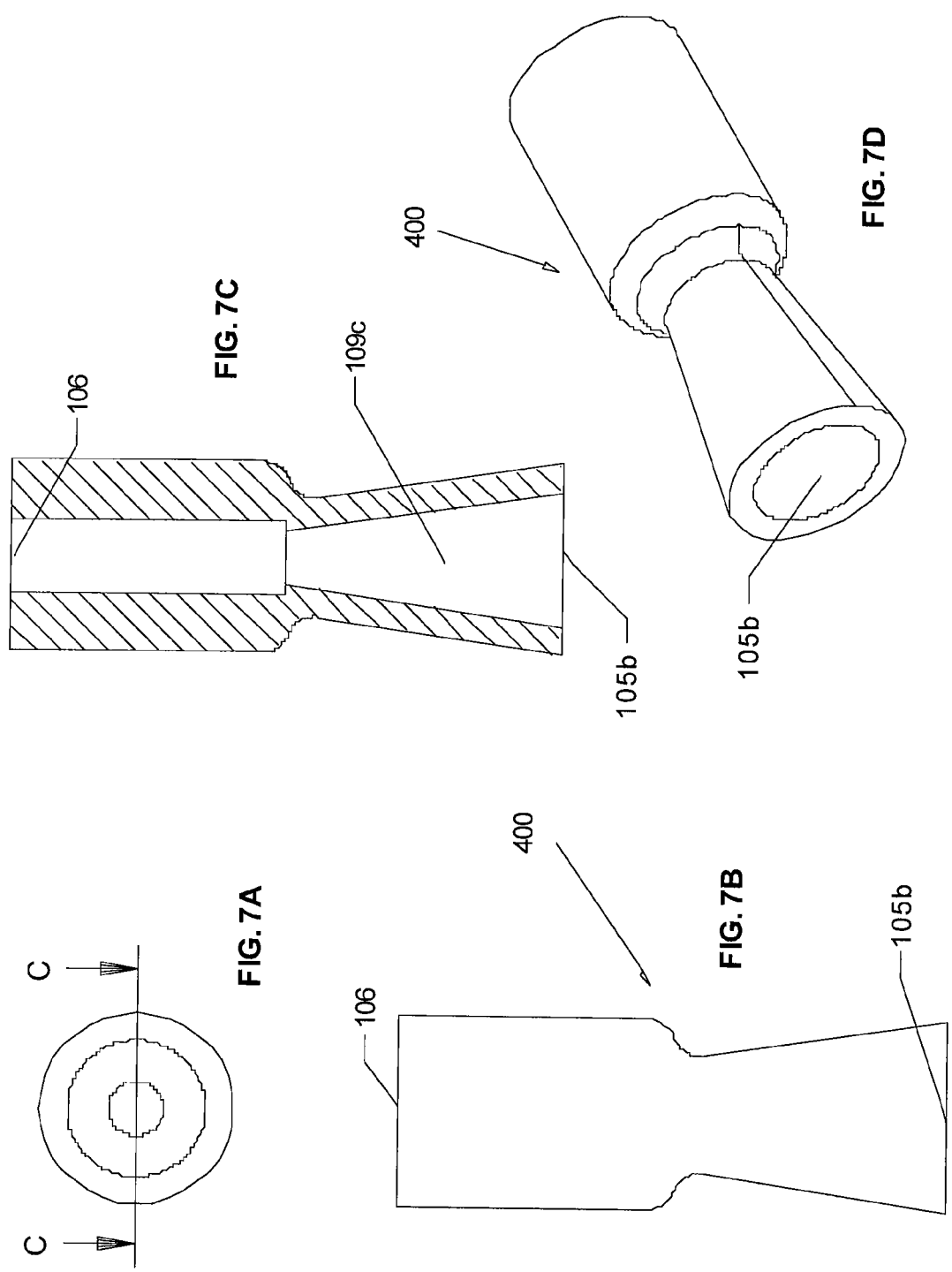

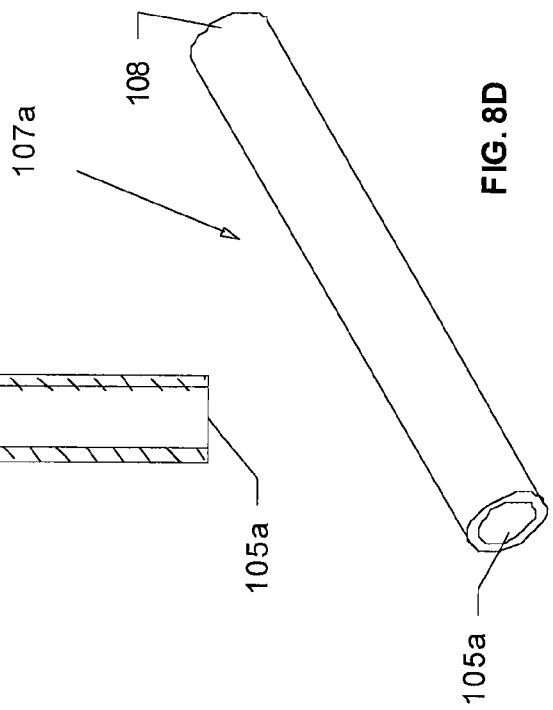
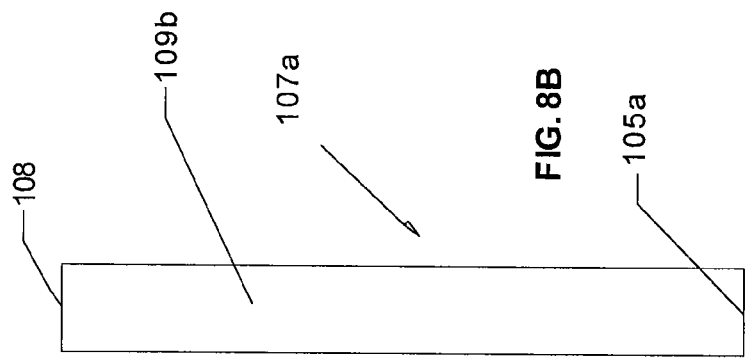

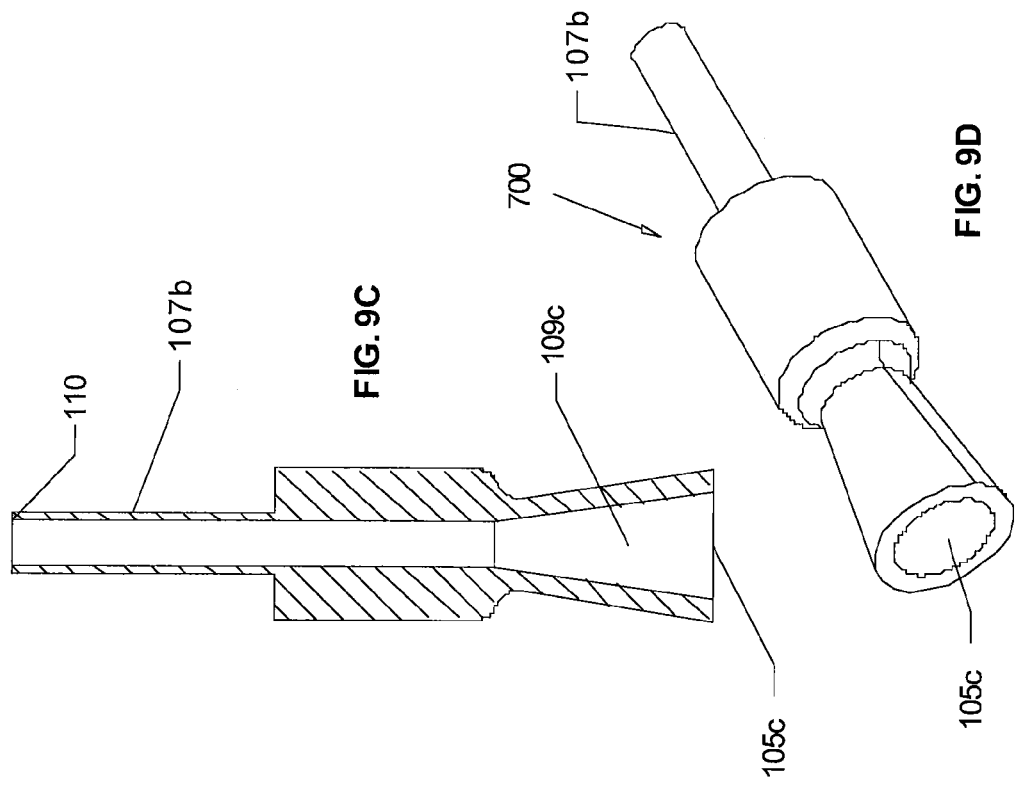
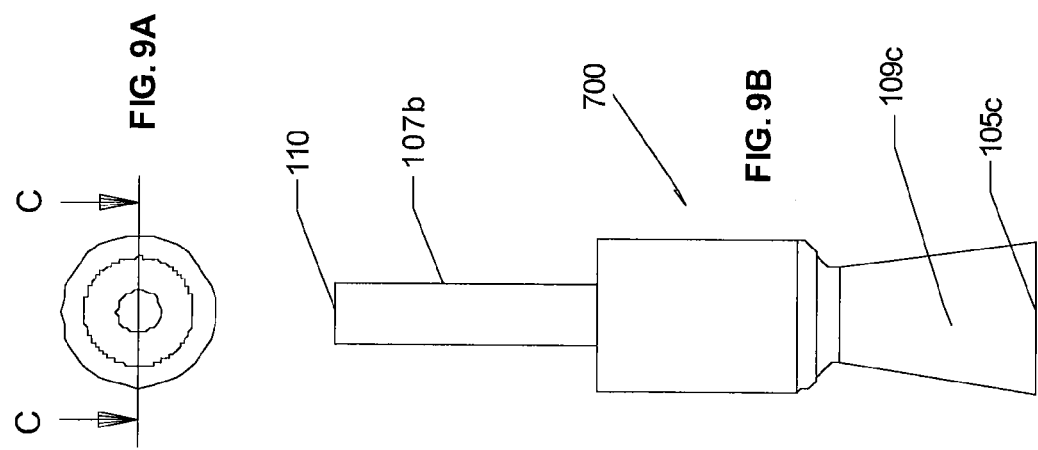

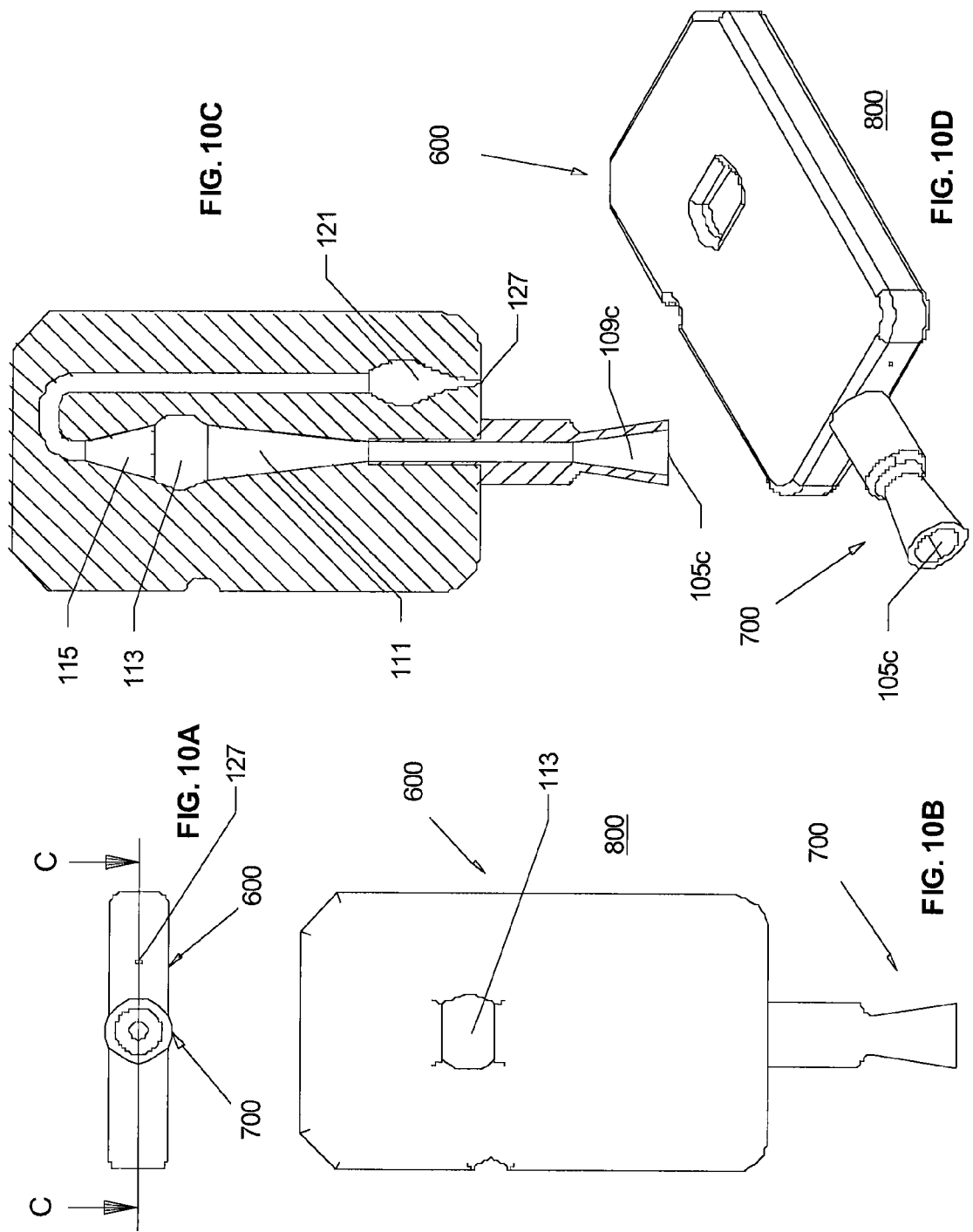

SPECTROSCOPIC SAMPLE HOLDER

RELATED APPLICATIONS

This application is a continuation-in-part of U.S. patent application Ser. No. 11/103,619, filed Apr. 12, 2005, the entire contents of which are hereby incorporated by reference.

FIELD OF THE INVENTION

The invention relates to spectroscopic analysis of blood, and a disposable sample holder that protects the blood from atmospheric contamination.

BACKGROUND OF THE INVENTION

There are many medical diagnostic tests that require a blood sample. A venous blood sample is usually collected in a vacuum-filled tube and taken to a central laboratory for analysis. In most cases the venous blood has to be centrifuged to obtain plasma, and the plasma is tested. In circumstances where arterial blood is needed, the blood is collected in a syringe from an artery or an arterial line (i.e., a tube connected to an artery), and the blood is taken to a central laboratory for analysis. Alternatively, much smaller blood samples (e.g. in the range of micro-liters) can be obtained using a pinprick and then a capillary tube that is inserted into a drop of blood that oozes onto the skin surface from the pin prick. Blood from the drop flows into the capillary tube as a result of capillary action. Blood from a pin prick flows out of capillaries, and hence is called capillary blood.

Babies cannot always provide an arterial blood sample, because the blood loss can affect their health. As a substitute, capillary blood can become "arterialized" by applying a heating pad to a baby's skin at the site chosen for the pinprick. The heat increases the blood flow in the area and the resulting capillary blood is similar in composition to arterial blood.

Point-of-care testing or near-patient testing is a process of testing the patient's blood near the patient. Point-of-care testing has many advantages, but analyzers that provide point-of-care testing are only available for a limited number of tests.

One example of a blood analysis technique that requires arterial blood or "arterialized" capillary blood is co-oximetry. Co-oximetry is a spectroscopic technique that can be used to measure the different Hemoglobin (Hb) species present in a blood sample. The results of co-oximetry can be further evaluated to provide Hb Oxygen Saturation ($sO_2$) measurements. Preferably, Hb $sO_2$ is measured from arterial blood, since arterial blood provides an indication of how well venous blood is oxygenated in the lungs. If the blood sample is exposed to air the Hb $sO_2$ measurements are falsely elevated, as oxygen from the air is absorbed into the blood sample. Moreover, the presence of small air bubbles trapped inside the capillary tube also lead to analysis errors, because the partial pressure of oxygen in the sample rises. Evidence of this is found in the *Tietz Textbook of Clinical Chemistry*, 3rd ed. (ISBN: 0721656102); which describes a representative example of how a 100 micro-liters air-bubble causes a 4 mm of mercury increase in the partial pressure of oxygen in a 2 ml blood sample. It is commonly understood that this effect increases as the ratio of blood sample volume to air volume decreases.

A sample holder referred to as a "Sample Tab" is described in U.S. Pat. No. 6,841,132 and U.S. Pat. No. 7,108,833 for use in point-of care testing. The Sample Tab, which comprises a well and a hinged-cover, can also be used in the central laboratory. The major drawback of the Sample Tab is that the blood is exposed to the atmosphere, and consequently cannot be used to measure blood oxygenation. Also, the well of the Sample Tab is difficult to fill when the blood comes directly from a pinprick. The present invention overcomes some of the limitations of the Sample Tab.

SUMMARY OF THE INVENTION

According to an aspect of an embodiment of the invention there is provided a sample holder comprising: (a) a housing having a width dimension and a depth dimension orthogonal to the width dimension, (b) an inlet transition chamber, in the housing, for receiving blood to be analyzed, (c) an optical chamber, in the housing, defining a void for receiving the blood from the inlet transition chamber, the optical chamber having at least one optical window for spectroscopic analysis of the blood and an optical chamber depth extending from the at least one optical window parallel to the depth dimension, wherein an optical chamber width parallel to the width dimension is greater than the optical chamber depth, (d) an overflow chamber, in the housing, for receiving the blood from the optical chamber, and (e) an outlet vent, in the housing and fluidly connected to the overflow chamber, to provide an outflow path for air, and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber.

According to another aspect of an embodiment of the invention there is provided a sample holder comprising: (a) a housing having a width dimension and a depth dimension orthogonal to the width dimension, (b) an inlet for receiving blood to be analyzed, the inlet comprising a piece of capillary tube, wherein the piece of capillary tube is an integral part of the housing, (c) an inlet transition chamber, in the housing, for receiving the blood from the inlet, (d) an optical chamber, in the housing, for receiving the blood from the inlet transition chamber, the optical chamber having at least one optical window for spectroscopic analysis of the blood and an optical chamber depth extending from the at least one optical window parallel to the depth dimension, (e) an overflow chamber, in the housing, for receiving the blood from the optical chamber, and (f) an outlet vent, in the housing, and fluidly connected to the overflow chamber, to provide an outflow path for air, and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber. In some embodiments of the invention, the optical chamber defines a void and an optical chamber width parallel to the width dimension is greater than the optical chamber depth.

According to yet another aspect of an embodiment of the invention there is provided a sample holder comprising: (a) a housing having a width dimension and a depth dimension orthogonal to the width dimension, (b) an inlet, in the housing, for receiving blood from a syringe to be analyzed, wherein the inlet is configured to engage the syringe, (c) an inlet transition chamber, in the housing, for receiving the blood from the inlet, (d) an optical chamber, in the housing, defining a void for receiving the blood from the inlet, the optical chamber comprising at least one optical window for spectroscopic analysis of the blood and an optical chamber depth extending from the at least one optical window parallel to the depth dimension, wherein an optical chamber width parallel to the width dimension is greater than the optical chamber depth, (e) an overflow chamber, in the housing, for receiving the blood from the optical chamber, (f) a buffer chamber for collecting an excess of the blood from the overflow chamber, and (g) an outlet vent, in the housing and fluidly connected to the overflow chamber, to provide an outflow path for air, and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber.

According to still yet another aspect of an embodiment of the invention there is provided a sample holder assembly comprising: (a) a sample holder having (i) a housing having a width dimension and a depth dimension orthogonal to the width dimension, (ii) an inlet, in the housing, for receiving blood to be analyzed, (iii) an inlet transition chamber, in the housing, for receiving blood from the inlet, (iv) an optical chamber, in the housing, defining a void for receiving the blood from the inlet, the optical chamber comprising at least one optical window for spectroscopic analysis of the blood and an optical chamber depth extending parallel to the depth dimension from the at least one optical window parallel to the depth dimension, wherein an optical chamber width parallel to the width dimension is greater than the optical chamber depth, and (v) an outlet vent, in the housing and fluidly connected to the optical chamber, to provide an outflow path for air, and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber, and (b) an adaptor, wherein the adaptor is fluidly connected to the inlet to receive the blood from a source. In some embodiments of the invention, the adaptor comprises an adaptor outlet for mating with the inlet in the housing, and an adaptor inlet for receiving the blood from the source, wherein the adaptor inlet is fluidly connected to the optical chamber. In some further embodiments of the invention, the adaptor inlet and the adaptor outlet are defined by the ends of a piece of capillary tube. In yet some further embodiments of the invention, the adaptor inlet is configured to accept a syringe.

Other aspects and features of the present invention will become apparent, to those ordinarily skilled in the art, upon review of the following description of the specific embodiments of the invention.

BRIEF DESCRIPTION OF THE DRAWINGS

For a better understanding of the present invention, and to show more clearly how it may be carried into effect, reference will now be made, by way of example, to the accompanying drawings, which illustrate aspects of embodiments of the present invention and in which:

FIG. 1A is a schematic drawing showing a front view of a sample holder suitable for measurement of a blood sample according to a first embodiment of the invention;

FIG. 1B is a schematic drawing showing a top view of the sample holder shown in FIG. 1A;

FIG. 1C is a cross-sectional view through the sample holder shown in FIG. 1B along line C-C;

FIG. 1D is an alternative cross-sectional view through the sample holder shown in FIG. 1A along line D-D;

FIG. 1E is an alternative cross-sectional view through the sample holder shown in FIG. 1B along line E-E;

FIG. 1F is a perspective view of the sample holder shown in FIG. 1A, with an optional capping apparatus 150;

FIG. 1G is the top view of the sample holder shown in FIG. 1B, with indicating lines for alternative cross-sectional views;

FIG. 1H is an alternative cross-sectional view through the sample holder shown in FIG. 1G along line H-H;

FIG. 1J is an alternative cross-sectional view through the sample holder shown in FIG. 1G along line J-J;

FIG. 1K is an alternative cross-sectional view through the sample holder shown in FIG. 1G along line K-K;

FIG. 1L is an alternative perspective view of the sample holder shown in FIG. 1A;

FIG. 1M is the top view of the sample holder shown in FIG. 1B, with optional guide lines for filling;

FIG. 2A is a schematic drawing showing a front view of a sample holder suitable for measurement of a blood sample according to a second embodiment of the invention;

FIG. 2B is a schematic drawing showing a top view of the sample holder shown in FIG. 2A;

FIG. 2C is a cross-sectional view through the sample holder shown in FIG. 2B along line C-C;

FIG. 2D is an alternative cross-sectional view through the sample holder shown in FIG. 2A along line D-D;

FIG. 2E is an alternative cross-sectional view through the sample holder shown in FIG. 2B along line E-E;

FIG. 2F is a perspective view of the sample holder shown in FIG. 2A;

FIG. 2G is the top view of the sample holder shown in FIG. 2B, with optional guide lines for filling and an optional cap 250;

FIG. 2H is the perspective view of the sample holder shown in FIG. 2F, with an optional cap 250;

FIG. 2J is an alternative cross-sectional view through the sample holder shown in FIG. 2G along line J-J;

FIG. 3A is a perspective view of an analyzer that uses the sample holders shown in FIGS. 1A-1M and FIGS. 2A-2J, with a sample holder 200 inserted in the analyzer;

FIG. 3B is a front view of the analyzer shown in FIG. 3A;

FIG. 3C is a cross-sectional view through the analyzer shown in FIG. 3B along line C-C;

FIG. 3D is an alternative cross-sectional view through the analyzer shown in FIG. 3B along line D-D;

FIG. 3E is a detailed view of the detail E shown in FIG. 3C.

FIG. 4A is a schematic drawing showing a front view of a sample holder suitable for measurement of a blood sample according to a third embodiment of the invention;

FIG. 4B is a schematic drawing showing a top view of the sample holder shown in FIG. 4A;

FIG. 4C is a cross-sectional view through the sample holder shown in FIG. 1A along line C-C;

FIG. 4D is a perspective view of the sample holder shown in FIG. 4A;

FIG. 5A is a schematic drawing showing a front view of a sample holder suitable for measurement of a blood sample according to a fourth and fifth embodiment of the invention;

FIG. 5B is a schematic drawing showing a top view of the sample holder shown in FIG. 5A;

FIG. 5C is a cross-sectional view through the sample holder shown in FIG. 5A along line C-C;

FIG. 6A is a schematic drawing showing a front view of a sample holder suitable for measurement of a blood sample according to the fourth embodiment of the invention;

FIG. 6B is a schematic drawing showing a top view of the sample holder shown in FIG. 6A;

FIG. 6C is a cross-sectional view through the sample holder shown in FIG. 6A along line C-C;

FIG. 7A is a schematic drawing showing a front view of a first example of an adaptor for a sample holder suitable for measurement of a blood sample according to the third embodiment of the invention;

FIG. 7B is a schematic drawing showing a top view of the adaptor shown in FIG. 7A;

FIG. 7C is a cross-sectional view through the adaptor shown in FIG. 7A along line C-C;

FIG. 7D is a perspective view of the adaptor shown in FIG. 7A;

FIG. 8A is a schematic drawing showing a front view of a second example of an adaptor for a sample holder suitable for measurement of a blood sample according to the fourth embodiment of the invention;

FIG. 8B is a schematic drawing showing a top view of the adaptor shown in FIG. 8A;

FIG. 8C is a cross-sectional view through the adaptor shown in FIG. 8A along line C-C;

FIG. 8D is a perspective view of the adaptor shown in FIG. 8A;

FIG. 9A is a schematic drawing showing a front view of a third example of an adaptor for a sample holder suitable for measurement of a blood sample according to a fifth embodiment of the invention;

FIG. 9B is a schematic drawing showing a top view of the adaptor shown in FIG. 9A;

FIG. 9C is a cross-sectional view through the syringe adaptor shown in FIG. 9A along line C-C;

FIG. 9D is a perspective view of the adaptor shown in FIG. 9A;

FIG. 10A is a schematic drawing showing a front view of a sample holder suitable for measurement of a blood sample according to the fifth embodiment of the invention;

FIG. 10B is a schematic drawing showing a top view of the sample holder shown in FIG. 10A;

FIG. 10C is a cross-sectional view through the sample holder shown in FIG. 10A along line C-C; and FIG. 10D is a perspective view of the sample holder shown in FIG. 10A;

DETAILED DESCRIPTION OF PREFERRED ASPECTS OF THE INVENTION

One embodiment of the invention provides one sample holder that is suitable for both the collection and analysis (sometimes referred to as measurement) of a blood sample. The sample is analyzed by spectroscopic means, which is also referred to as spectroscopy. Once a blood sample is drawn into such a sample holder the blood sample can be analyzed, without having to transfer any portion of the blood sample into another vessel. The sample holder is provided with an optical chamber that is specifically designed to spread blood into a thin film, thereby reducing the incidences of trapped air bubbles in the blood sample collected in the optical chamber, and allowing sufficient electromagnetic radiation (EMR) to emerge from the blood sample for spectroscopic analysis. Air bubbles are pushed through the optical chamber and guided out of the sample holder through a vent. Because the blood in the optical chamber is a thin film, the average attenuation of EMR caused by scattering of the EMR by red blood cells in a blood sample, is minimized without having to hemolyze the red blood cells. Red blood cells are usually hemolyzed using sound waves or reagents. Moreover, because in some embodiments of the invention the blood sample collection and measurement can be performed rapidly, the addition of an anticoagulant is not required to prevent clotting.

Blood within the optical chamber is further isolated from contamination by room air by providing an inlet transition chamber and an overflow chamber at a respective entrance and exit of the optical chamber. In use, blood in the inlet transition chamber and the overflow chamber serve as respective barriers between blood in the optical chamber and room air, thereby isolating the blood in the optical chamber from oxygen contamination. In the incident of trapped air bubbles, those skilled in the art will appreciate that various known calibration algorithms for many specific analytes measured in the blood sample can be used to compensate for the inclusion of trapped air bubbles, except for those analytes such as the partial pressure of oxygen and oxy-hemoglobin, which become falsely elevated as a result of oxygen introduced into the blood sample from the air bubbles.

In some embodiments the sample holder includes at least one visible fill line or indicator serving as a marker providing a user with a visual indicator relating to the sufficiency of the blood sample in the optical chamber. Briefly, in some embodiments, the visible fill line is located in a position in and/or beyond the overflow chamber that is indicative of whether or not a volume of blood drawn into the sample holder is present in sufficient amount to: i) ensure that the blood in the optical chamber is substantially free from contaminants that may have been introduced during the collection of the blood sample; and/or, ii) ensure that there is an effective amount of blood surrounding the optical chamber to isolate the blood in the optical chamber from room air. In some embodiments, a first fill line is located in the outflow chamber, before a capillary break, and a second fill line is located in the capillary break.

In accordance with an embodiment of the invention, a very specific example of a sample holder suitable for the collection and measurement of a blood sample is shown in FIGS. 1A-1M. Specifically, FIG. 1A is a schematic drawing illustrating the front view of a sample holder 100; FIG. 1B is a top view of the sample holder 100 shown in FIG. 1A; FIG. 1C is a cross-sectional view through the sample holder shown in FIG. 1B along line C-C; FIG. 1D is an alternative cross-sectional view through the sample holder shown in FIG. 1A along line D-D; FIG. 1E is an alternative cross-sectional view through the sample holder shown in FIG. 1B along line E-E; FIG. 1F is a perspective view of the sample holder shown in FIG. 1A, with an optional capping apparatus 150; FIG. 1G is the top view of the sample holder as shown in FIG. 1B, with indicating lines for alternative cross-sectional views; FIG. 1H is an alternative cross-sectional view through the sample holder shown in FIG. 1G along line H-H; FIG. 1J is an alternative cross-sectional view through the sample holder shown in FIG. 1G along line J-J; FIG. 1K is an alternative cross-sectional view through the sample holder shown in FIG. 1G along line K-K; FIG. 1L is an alternative perspective view of the sample holder shown in FIG. 1A with an optional capping apparatus 150; and FIG. 1M is the top view of the sample holder shown in FIG. 1B, with optional guide lines 119a and 119b for filling, also referred to as fill lines.

The sample holder 100 includes a housing 123 defining an internal volume between an inlet opening 105 and an outlet vent 127. As shown in FIGS. 1B, 1C and 1D respectively, the housing 123 has a side dimension s, a depth dimension d, and a width dimension w. The internal volume includes three distinct portions including an inlet transition chamber 111, an optical chamber 113 and an overflow chamber 115 that are fluidly connected in series. The inlet transition chamber 111 is fluidly connected between the optical chamber 113 and the inlet opening 105. In this particular embodiment a short protruding length of capillary tube 107 defines an inlet 109 for the sample holder 100, and the inlet 109 extends into fluid connection with the inlet transition chamber 111 from the inlet opening 105. Those skilled in the art will appreciate that the inlet 109 can be considered to be an extension of the inlet transition chamber 111.

In some embodiments of the invention, for example sample holder (or apparatus) 500 shown in FIGS. 4A-4D, the portion of the apparatus housing the inlet opening 105 (FIGS. 1A-1B), i.e., the capillary tube 107, is referred to as an inlet. In sample holder 500, capillary tube 107 is considered as an inlet, since it receives a female adaptor 400. In the case of apparatus 600 shown in FIGS. 5A-5C, the inlet is labeled 109a, and it can receive a male adaptor, as will be described later.

The overflow chamber 115 is fluidly connected between the optical chamber 113 and the outlet vent 127. In this particular embodiment, a J-shaped channel 117 referred to as an outflow chamber, connects the overflow chamber 115 to the outlet vent 127. Those skilled in the art will appreciate that the outflow chamber does not have to be J-shaped, because the vent 127 can be located in other positions in the housing 123 as illustrated in U.S. patent application Ser. No. 11/103,619. Furthermore, those skilled in the art will also appreciate that the outflow chamber 117 can be considered to be an extension of the overflow chamber 115. One advantage of this particular embodiment is that the two open ends of the sample holder 100 remain outside the analyzer 300 (illustrated in FIGS. 3A-3E) during use. This feature prevents the sample holder receptor 340 (shown in FIGS. 3B, 3C and 3D) from becoming contaminated with blood, in the event that blood leaks out of the inlet opening 105 or the outlet vent 127. With specific reference to FIG. 1B, respective optically transparent (or translucent) top and bottom wall-portions 113a and 113b of the housing 123 define the optical chamber 113. Further, in this preferred embodiment, the top and bottom wall-portions 113a and 113b are recessed with respect to the corresponding top and bottom surfaces 123a and 123b of the housing 123 in order to protect the exterior faces of the top and bottom wall-portions 113a and 113b from scratches, although those skilled in the art will appreciate that this is not essential. In some embodiments, the interior walls of the sample holder are also treated with a hydrophilic coating to promote even spreading of the blood within the optical chamber 113. Those skilled in the art will appreciate that the wall-portions 113a and 113b do not have to be completely parallel to each other, and furthermore, the interior and exterior surfaces of either wall-portion 113a or wall-portion 113b do not have to be completely parallel.

The interior of the optical chamber 113 is designed to evenly spread blood into a thin film free of air bubbles. Briefly, in use, a thin film of blood completely filling the optical chamber 113 is suitable for spectroscopic analysis through the top and bottom wall-portions 113a and 113b respectively.

Referring to FIG. 1C, the sample holder 100 is provided with a tapered overflow chamber 115 in fluid connection with a cylindrical outflow chamber 117, but in some embodiments, the depth of the overflow chamber remains approximately uniform, and the overflow chamber makes direct fluid connection with the outlet vent 127.

Referring to FIGS. 1B, 1D, 1E, 1K and 1M, the apparatus 100, in some embodiments, is provided with an optional capillary break 121. The capillary break 121 is a portion of the outflow chamber 117, where the cross-sectional area along a plane parallel to the width dimension and the depth dimension, is larger than the largest cross-sectional area of the overflow chamber along a plane parallel to the width dimension and the depth dimension, such that the opening is too large to sustain the flow by capillary action. In this particular embodiment, the flow cannot be sustained beyond the fill line 119b, shown in FIG. 1M. Blood flow begins to decrease significantly after the blood enters the capillary break 121, therefore the user doesn't have to be concerned about overfilling the sample holder 100. The other optional fill line 119a, shown in FIG. 1M, is positioned to indicate that as long as the blood flows past the fill line 119a, the sample holder 100 is sufficiently filled, and the user no longer has to be concerned about underfilling the sample holder 100. Therefore, in some embodiments, the sample holder is provided with fill line 119a and not fill line 119b, if the embodiment comprises a capillary break 121. In such an embodiment where there is a single fill line (119a), the instruction, "Fill Between Lines" is replaced with the instruction, "Fill Past Line," as illustrated in FIG. 2G. Those skilled in the art will appreciate that although a circular cross-section of the capillary break 121 is shown in FIG. 1K, other shapes may be used, for example without any limitations, an oval shape. In the embodiment illustrated in FIG. 2G, the sample holder 200 could be filled with blood from a syringe, by engaging the male end of the syringe with the inlet 109. In such a situation, capillary action is not essential for blood flow, and the chamber 121, although it is referred to as a capillary break, chamber 121 actually provides a buffer for excess blood beyond the fill line 119a. Therefore, in some embodiments, the chamber 121 is described as a buffer chamber. The buffer chamber 121 minimizes the likelihood that blood will escape through the outlet vent 127 and contaminate the user and the analyzer. In this specific embodiment, the buffer chamber 121 is a portion of the outflow chamber 117, where the cross-sectional area along a plane parallel to the width dimension and the depth dimension, is larger than the largest cross-sectional area of the overflow chamber along a plane parallel to the width dimension and the depth dimension. Those skilled in the art will appreciate that the buffer chamber could be a long narrow chamber in the shape of a coil, of sufficient volume to accommodate the excess blood.

With further specific reference to FIGS. 1C and 1D, the interior of optical chamber 113 is much thinner in depth than the diameter of the inlet 109 and the broad end of the inlet transition chamber 111. In some embodiments, the depth of the optical chamber 113, being the internal distance between the respective interior faces of the top and bottom wall-portions 113a and 113b, ranges from approximately 0.02 mm to 0.2 mm, whereas the diameter of the inlet 109 is about 0.5 mm to 2.0 mm. Light scattering caused by red blood cells is more prevalent and damaging to measurement accuracy when the depth of the optical chamber 113 is more than 0.1 mm, and so a depth of less than 0.1 mm is preferred. If the depth is less than 0.02 mm the natural viscosity of blood may reduce how effectively blood can be spread evenly through the optical chamber 113. Moreover, with further reference to FIG. 1B, the width-wise span of the optical chamber 113 is wider than the diameter of the inlet 109 and is substantially equal to or larger than the broad end of the inlet transition chamber 111. Specifically, the width-wise span of the optical chamber 113 ranges, without limitation, between approximately 2 to 10 mm. Taken together the dimensions of the optical chamber 113 preferably result in an approximate volume of less than 2 micro-liters. Although this particular embodiment of the invention shows a cylindrical inlet 109 and a cylindrical outflow 117, and cylindrical shapes are preferred, these chambers of the sample holder 100 or 200 are not limited to cylindrical shapes.

Referring to FIGS. 1B and 1D, the inlet transition chamber 111 is provided to serve as a transition between the inlet opening 105 and the optical chamber 113 and a barrier between room air and blood in the optical chamber 113. As noted above, the capillary tube 107 defines the inlet 109, and in some embodiments, the capillary tube 107 is the inlet. In the preferred embodiment, the inlet transition chamber 111 is tapered towards the optical chamber 113 so as to have a diminishing depth and an increasing width relative to the diameter of the inlet 109 in the direction of the optical chamber 113 from the inlet 109. Moreover in use, blood remaining in the inlet transition chamber 111 serves as a barrier between room air and the blood in the optical chamber 113 through which air cannot easily diffuse toward the blood in the optical chamber 113.

Still referring to FIGS. 1B and 1D, the overflow chamber 115 is similarly provided to serve as a transition between the outlet vent 127 and the optical chamber 113 and a barrier between room air and blood in the optical chamber 113 during operation. In this particular embodiment, the overflow chamber 115 has a complementary design to that of the inlet transition chamber 111. That is, the overflow chamber 115 is flared away from the optical chamber 113 so as to have an increasing depth and a decreasing width in the direction away from the optical chamber 113. In some embodiments, the depth of the overflow chamber remains uniform. The depths of the overflow chamber 115 increase toward the outflow chamber 117, and preferably exceed 2 mm at the capillary break 121. In this particular embodiment, the volume of the overflow chamber 115 is larger than that of the optical chamber 113, and during operation, filling the overflow chamber 115 ensures that blood in the optical chamber is substantially free from contamination and effectively isolated from room air that may enter via the outlet vent 127. In terms of total volume, the overflow chamber 115 has a volume that is preferably greater than the volume of the optical chamber 113.

Referring to FIGS. 1F and 1L, the sample holder 100, in some embodiments, is provided with a capping apparatus 150. The capping apparatus is provided with a cap 145, a tether 143 and a ring connector 141. The cap 145 is connected to the ring connector 141 by the tether 143, thereby connecting the cap 145 to the sample holder 100. The ring connector 141 is sized to fit securely around the piece of capillary tube 107. One function of the cap 145 is to prevent contamination of the user and the analyzer 300 (FIG. 3A) with blood.

Referring to FIGS. 1B, 1D, 1F, 1G, 1L and 1M, the sample holder 100 is provided with a notch 125 for locating the sample holder 100 inside the receptor 340 of the analyzer 300, illustrated in FIG. 3D. Those skilled in the art will appreciate that the notch 125 is not essential for the function of the sample holder 100 or 200.

Before the sample holder 100 is employed during a blood test, room air is present within the internal volume (i.e. within the inlet transition chamber 111, the optical chamber 113, and the overflow chamber 115, etc.). Particularly, the room air contains 20% oxygen that could contaminate a relatively small blood sample drawn into the sample holder 100. However, when the sample holder is used properly, blood within the optical chamber 113 is substantially free from oxygen contamination. Moreover, the addition of a hemolyzing agent or an anticoagulant to ensure that the blood sample in the optical chamber is suitable for spectroscopic analysis is not required. Specifically, in operation, the inlet opening 105 is inserted into a blood drop. Blood flows through the inlet 109 as a result of capillary action. The leading surface of the inflowing blood is exposed to the room air within the sample holder 100, which is simultaneously being forced out of the outlet vent 127 by the inflow of blood. The outlet vent 127 provides a flow path for the room air that moves away from the inflow of blood. Without the vent outlet 127, flow would be impeded and room air would flow back through the inflowing blood, thereby contaminating the blood sample and possibly leaving air bubbles within the sample holder 100. Eventually, enough blood enters the sample holder 100 to fill the overflow chamber 115, thereby forcing room air out of the sample holder 100 through the outlet vent 127. Any blood that was exposed to the room air during the filling process is in the overflow chamber 115 and not within the optical chamber 113 and internal pressure prevents back flow of the blood. Thus, any contaminated blood, from the leading surface of the blood during the filling stage, is expected to remain in the overflow chamber 115. As noted previously, the blood in the inlet transition chamber 111 and the blood in the overflow chamber 115 effectively isolate the blood in the optical chamber 113 from further contamination from the room air. Once the blood is collected in the sample holder, it is ready for measurement by inserting the sample holder into a receptor 340 shown in FIGS. 3B, 3C and 3D, as a non-limiting example. Care must be taken to keep the inlet opening 105 submerged in the blood drop, to avoid drawing air into the sample holder. The blood drawn into the sample holder must come from inside the blood drop. During the short period of the procedure, the outer layer of the blood drop that is exposed to the air sufficiently protects the blood inside the drop from atmospheric contamination.

In accordance with a second embodiment of the invention, a very specific example of a sample holder 200 suitable for the measurement of a blood sample is shown in FIGS. 2A-2J. Specifically, FIG. 2A is a schematic drawing showing a front view of a sample holder 200; FIG. 2B is a schematic drawing showing a top view of the sample holder shown in FIG. 2A; FIG. 2C is a cross-sectional view through the sample holder shown in FIG. 2B along line C-C; FIG. 2D is an alternative cross-sectional view through the sample holder shown in FIG. 2A along line D-D; FIG. 2E is an alternative cross-sectional view through the sample holder shown in FIG. 2B along line E-E; FIG. 2F is a perspective view of the sample holder shown in FIG. 2A; FIG. 2G is the top view of the sample holder shown in FIG. 2B, with an optional guide line 119a for filling and an optional cap 250; FIG. 2H is a perspective view of the sample holder shown in FIG. 2G, with the optional cap 250; and FIG. 2J is an alternative cross-sectional view through the sample holder shown in FIG. 2G along line J-J.

The sample holder 200 illustrated in FIGS. 2A-2J is similar to the sample holder 100 illustrated in FIGS. 1A-1M, and accordingly, elements common to both share common reference numerals. The primary difference, illustrated in FIGS. 2B, 2C, 2D and 2F is that the piece of capillary tube 107 that defines the inlet 109 (FIG. 1B-1D) has been replaced with a flared inlet 109 (FIGS. 2C, 2D, 2G and 2J). The inlet opening 105 is large enough to accommodate the male end of a syringe. The sample holder 200 is well suited for scenarios where blood from a syringe is available, for example in a cardiac catheterization lab, as blood can be passed directly from the syringe to the sample holder 200 without exposure to room air. Because of the relatively large inlet opening 105, the sample holder 200 is also well suited for squeezing blood directly into the sample holder 200 by placing the inlet opening 105 over the pin prick. In such a case, a drop of blood does not necessarily have to be formed at the pin-prick site. Therefore, sample holder 200 can also be used like sample holder 100, to collect blood as well as measure the blood sample by spectroscopic means. By covering the pin prick, fresh blood oozing out of the pin prick is protected from exposure to the atmosphere, and the blood that is exposed to the air inside the sample holder 200 is pushed into the overflow chamber 115.

A second difference is that the exterior of the optical chamber 113 is circular, whereas the exterior of the optical chamber 113 of the sample holder 100 is not circular. A third difference is that the side dimension s of the sample holder 200 is its full length, whereas the side dimension s of the sample holder 100 does not include the length of the piece of capillary tube 107. The side dimension s is mostly determined by the depth of the analyzer receptor 340, illustrated in FIG. 3D.

The inlet opening 105 of the apparatus 100 is housed in a piece of capillary tube 107 that is referred to, in some embodiments, as an inlet (more accurately, a male inlet), whereas the inlet opening 105 is housed in a female inlet 109 in apparatus 200. The term male inlet is used to indicate that the inlet can be inserted into the source of blood (e.g., a drop of blood on the skin) for filling the apparatus, and the term female inlet is used to indicate that the source of blood can be inserted into the female inlet for filling the apparatus (e.g., a syringe containing blood). Other embodiments of the invention are described where adaptors are used to convert a male inlet into a female inlet, and vice versa. Those skilled in the art will appreciate that although this aspect of the invention is not essential to the invention, it is useful for the manufacturing processes, and adds versatility to the invention. The adaptors 400, 107a, and 700 are three examples that can be used to alter the configuration of the inlet 105d of the apparatus 500, so that the sample holder can receive blood from any source, for example without any limitations, a drop of blood on the skin of a body part after a pin prick, and blood in a syringe. Blood gases and Co-oximetry are frequently measured on blood drawn into a syringe from an arterial line. Although the intended use of the present invention is to perform spectroscopic measurement on a blood sample protected from atmospheric contamination, it will be obvious that the sample holders can be used for spectroscopic measurement of other liquid samples, and the uses are not limited to the intended use.

A third difference is, as mentioned previously, the chamber 121 is a capillary break in one aspect of the invention, but in another aspect of the invention (for example when blood is forced into the sample holder 200 from a syringe, or from a pin prick by slightly squeezing the body part containing the pin prick), chamber 121 is described as a buffer chamber for collecting excess blood. When blood is forced through the inlet 109, the buffer chamber 121 collects any blood that overshoots the fill line 119a, and leakage of blood through the outlet vent 127 is avoided.

Referring to FIGS. 2G, 2H, and 2J, the sample holder 200, in some embodiments, is provided with a cap 250. One function of the cap 250 is to prevent contamination of the user and the analyzer with blood.

With respect to spectroscopic measurements, the examples shown describe a sample holder that operates in transmission mode. Those skilled in the art will appreciate that the spectroscopic sample holders can also operate in reflectance mode by placing a reflecting member on one side of the optical chamber 113, such that the EMR transmitted through the sample would be reflected off the reflecting member, and the reflected EMR would enter the sample for the second time. In an analyzer operating in the reflectance mode, both the EMR source and the photodetector would be on the same side of the optical chamber 113. Moreover, those skilled in the art will also appreciate that instead of using a reflecting member in the analyzer, one side of the wall-portions (113a or 113b) of the optical chamber 113 could be coated with a reflecting material.

As a non-limiting example, a spectroscopic analyzer that operates in transmission mode, which can accommodate sample holder 100 (shown in FIGS. 1A-1M) or sample holder 200 (shown in FIGS. 2A-2J), is illustrated in FIGS. 3A-3E. FIG. 3A is a perspective view of the analyzer with a sample holder 200 inserted into the receptor 340 of the analyzer 300; FIG. 3B is a front view of the analyzer 300 shown in FIG. 3A; FIG. 3C is a cross-sectional view through the analyzer 300 shown in FIG. 3B along line C-C; FIG. 3D is an alternative cross-sectional view through the analyzer 300 shown in FIG. 3B along line D-D; and FIG. 3E is a detailed view of the detail E shown in FIG. 3C. The sample holder 200 is provided with a notch 125, which is used for locating the sample holder 200 in the receptor 340 of the analyzer 300. Referring to FIG. 3D, shown is the notch 125 (illustrated in both sample holders 100 and 200), engaged in a spring-loaded projection (not shown) within the receptor 340 of the analyzer 300, for locating the sample holder in the proper position within the analyzer 300. Those skilled in the art will appreciate that the notch 125 is not essential and that there are other means of locating the sample holder within the analyzer. The spring-loaded projection within the receptor could also be a limit switch, which triggers the spectroscopic measurement process after the limit switch is compressed as the sample holder slides along the limit switch, and then released into the notch 125.

The analyzer 300 includes a housing 223 containing the various parts of a spectrometer, for example a receptor for accepting the sample, a source of EMR for irradiating the sample, a grating for dispersing the EMR emerging out of the sample into its component wavelengths, a photodetector for detecting the emerging EMR, electrical circuitry and a microprocessor (only the receptor and source of EMR are shown), which is well known to those in the field of spectroscopy, and for the sake of brevity, will not be described in details.

Referring to FIGS. 3A and 3B, the analyzer 300 is provided with a display screen 310 and a receptor 340 containing a sample holder 200, illustrated in details in FIGS. 2A-2J. Referring to FIG. 3B, the analyzer 300 is provided with three control buttons 320a, 320b and 320c. The locking mechanism for engaging the notch 125 in the sample holder 200 is not shown.

Referring to FIGS. 3B-3E, the analyzer 300 is provided with a source of EMR 350, an inlet aperture 360b for allowing EMR from the source 350 to irradiate the blood sample within the optical chamber 113 of the sample holder 200, and an outlet aperture 360a for allowing the EMR transmitted through the optical chamber 113 to impinge upon a photodetector (not shown). The detail E shown in FIG. 3C and shown as an enlarged view in FIG. 3E illustrates how the source of EMR is arranged to irradiate the blood sample in the optical chamber 113. In this example, the photodetector would be located above the receptor 340, adjacent to aperture 360a.

Referring to FIGS. 4A-4D, the apparatus 500 is an assembly of apparatus 100 shown in details in FIGS. 1A-1E, and 1G-1K, and an adaptor 400 shown in details in FIGS. 7A-7D, according to a third embodiment of the invention. FIG. 4A is a schematic drawing showing a front view of the sample holder 500; FIG. 4B is a schematic drawing showing a top view of the sample holder shown in FIG. 4A; FIG. 4C is a cross-sectional view through the sample holder shown in FIG. 1A along line C-C; and FIG. 4D is a perspective view of the sample holder shown in FIG. 4A. The adaptor 400 converts the male inlet 107 of apparatus 100 into a female inlet 109c. It will be obvious that apparatus 500 resembles apparatus 200 shown in FIGS. 2A-2J. The main difference is that the inlet 109c in apparatus 500 is projected away from the housing 123, whereas the inlet 109 in apparatus 200 is recessed in the housing 123 of apparatus 200. Those skilled in the art will appreciate that the adaptor 400 can include a Luer lock mechanism for engaging a syringe.

FIG. 7A is a schematic drawing showing a front view of the first example of an adaptor 400; FIG. 7B is a schematic drawing showing a top view of the adaptor shown in FIG. 7A; FIG. 7C is a cross-sectional view through the adaptor shown in FIG. 7A along line C-C; and FIG. 7D is a perspective view of the adaptor shown in FIG. 7A. The adaptor 400 is provided with an inlet opening 105b, an inlet 109c, and an opening 106 for engaging the adaptor 400 with the piece of capillary tube 107 of apparatus 100 shown in FIGS. 1B and 1E.

FIG. 5A is a schematic drawing showing a front view of a sample holder 600 suitable for measurement of a blood sample according to a fourth and fifth embodiment of the invention, which are described later. The sample holder 600 is provided with an inlet 109a that can receive one or more than one adaptor, which enables the sample holder to receive blood from any source, for example without any limitations, a drop of blood on the skin from a pinprick, or a syringe. Three examples of adaptors are provided as non-limiting examples. A first example was already shown in FIGS. 4A-4D, as adaptor 400. A second example is shown in detail in FIGS. 6A-6D, as adaptor 107a. It will be readily noticed that the adaptor 107a is a piece of capillary tube. The adaptor 107a is inserted through the opening 105d (FIGS. 5B-5C) to assemble the fourth embodiment of the invention 700, shown in FIGS. 6A-6C. It will be readily noticed that the apparatus 700 is the same as apparatus 100, except that it is an assembly of two parts. Those skilled in the art will appreciate that the sample holder 600 and the adaptor 107a can be frictionally engaged or held together by any means, including without any limitations, glue. FIG. 5B is a schematic drawing showing a top view of the sample holder 600 shown in FIG. 5A; and FIG. 5C is a cross-sectional view through the sample holder shown in FIG. 5A along line C-C. Preferably, apparatus 600 is manufactured in two halves that are mirror images of each other (one half is shown in FIG. 5C), and the appropriate adaptor affixed during or after the assembly of the two halves, to produce the embodiment with the desired means for receiving blood into the sample holder. Those skilled in the art will appreciate that there are different ways to manufacture the sample holders, and different ways to assemble the parts. As examples, without any limitation, the two halves like the part shown in FIG. 5C can be glued together or welded together.

FIG. 8A is a schematic drawing showing a front view of the second example of an adaptor 107a (also referred to as a piece of capillary tube or a capillary tube); FIG. 8B is a schematic drawing showing a top view of the adaptor shown in FIG. 8A; FIG. 8C is a cross-sectional view through the adaptor shown in FIG. 8A along line C-C; and FIG. 8D is a perspective view of the adaptor shown in FIG. 8A. Adaptor 107a is provided with an inlet opening 105a, an inlet 109b, and an outlet 108. It will be readily noticed that the openings 105a and 108 are identical.

FIG. 6A is a schematic drawing showing a front view of a sample holder 700 suitable for collection and measurement of a blood sample according to a fourth embodiment of the invention; FIG. 6B is a schematic drawing showing a top view of the sample holder shown in FIG. 6A; FIG. 6C is a cross-sectional view through the sample holder shown in FIG. 6A along line C-C; and FIG. 6D is a perspective view of the sample holder shown in FIG. 6A. Shown in FIG. 6C is the outlet 108 of the adaptor 107a (FIGS. 8A-8D), which provides fluid connection between the inlet opening 105a (FIGS. 8B-8D) and the inlet transition chamber 111 in apparatus 600.

Similarly, the fifth embodiment of the invention 800, shown in FIGS. 10A-10D, is an assembly of the apparatus 600 shown in FIGS. 5A-5C with a third example of an adaptor 700 shown in FIGS. 9A-9D. Those skilled in the art will appreciate that the sample holder 600 and the adaptor 700 can be held together by any means, for example without any limitations, frictional engagement or glue. It will be readily noticed that the apparatus 800 is similar to the apparatus 500, shown in FIGS. 4A-4D. Those skilled in the art will also appreciate that an apparatus like apparatus 800 can be made by assembling sample holder 600 (shown in FIGS. 5A-5C), adaptor 400 (shown in FIGS. 7A-7D), and adaptor 107a (shown in FIGS. 8A-8D).

FIG. 10A is a schematic drawing showing a front view of the sample holder 800; FIG. 10B is a schematic drawing showing a top view of the sample holder shown in FIG. 10A; FIG. 10C is a cross-sectional view through the sample holder shown in FIG. 10A along line C-C; and FIG. 10D is a perspective view of the sample holder shown in FIG. 10A.

FIG. 9A is a schematic drawing showing a front view of the third example of an adaptor 700 for a sample holder 800 shown in FIGS. 10A-10D; FIG. 9B is a schematic drawing showing a top view of the adaptor 700 shown in FIG. 9A; FIG. 9C is a cross-sectional view through the adaptor shown in FIG. 9A along line C-C; and FIG. 9D is a perspective view of the adaptor shown in FIG. 9A. The adaptor 700 is provided with an inlet opening 105c, and inlet 109c, and an outlet 110. The outlet 110 is housed in a piece of capillary tube 107b, which is an integral part of the adaptor 700. It will be readily noticed that the adaptor 700 can be made by frictionally engaging the adaptor 400 shown in FIGS. 7A-7D with the adaptor 107a shown in FIGS. 8A-8D, by passing the inlet opening 105a of adaptor 107a through the outlet 106 of the adaptor 400 shown in FIGS. 7A-7D.

While the above description provides example embodiments, it will be appreciated that the present invention is susceptible to modification and change without departing from the fair meaning and scope of the accompanying claims. Accordingly, what has been described is merely illustrative of the application of aspects of embodiments of the invention. Numerous modifications and variations of the present invention are possible in light of the above teachings. It is therefore to be understood that within the scope of the appended claims, the invention may be practiced otherwise than as specifically described herein.

The invention claimed is:

1. A sample holder comprising:
    a housing having a width dimension and a depth dimension orthogonal to the width dimension;
    an inlet transition chamber, in the housing, for receiving blood to be analyzed;
    an optical chamber, in the housing, defining a void for receiving the blood from the inlet transition chamber, the optical chamber having at least one optical window for spectroscopic analysis of the blood and an optical chamber depth extending from the at least one optical window parallel to the depth dimension, wherein an optical chamber width parallel to the width dimension is greater than the optical chamber depth;

an overflow chamber, in the housing, for receiving the blood from the optical chamber; and an outlet vent, in the housing and fluidly connected to the overflow chamber, to provide an outflow path for air; and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber.

2. A sample holder comprising:

a housing having a width dimension and a depth dimension orthogonal to the width dimension;

an inlet for receiving blood to be analyzed, the inlet comprising a piece of capillary tube, wherein the piece of capillary tube is an integral part of the housing;

an inlet transition chamber, in the housing, for receiving the blood from the inlet;

an optical chamber, in the housing, for receiving the blood from the inlet transition chamber, the optical chamber having at least one optical window for spectroscopic analysis of the blood and an optical chamber depth extending from the at least one optical window parallel to the depth dimension;

an overflow chamber, in the housing, for receiving the blood from the optical chamber; and an outlet vent, in the housing, and fluidly connected to the overflow chamber, to provide an outflow path for air; and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber.

3. A sample holder comprising:

a housing having a width dimension and a depth dimension orthogonal to the width dimension;

an inlet, in the housing, for receiving blood from a syringe to be analyzed, wherein the inlet is configured to engage the syringe;

an inlet transition chamber, in the housing, for receiving the blood from the inlet;

an optical chamber, in the housing, defining a void for receiving the blood from the inlet, the optical chamber comprising at least one optical window for spectroscopic analysis of the blood and an optical chamber depth extending from the at least one optical window parallel to the depth dimension, wherein an optical chamber width parallel to the width dimension is greater than the optical chamber depth;

an overflow chamber, in the housing, for receiving the blood from the optical chamber;

a buffer chamber for collecting an excess of the blood from the overflow chamber; and an outlet vent, in the housing and fluidly connected to the overflow chamber, to provide an outflow path for air; and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber.

4. A sample holder assembly comprising:

a sample holder having a housing having a width dimension and a depth dimension orthogonal to the width dimension;

an inlet, in the housing, for receiving blood to be analyzed;

an inlet transition chamber, in the housing, for receiving the blood from the inlet;

an optical chamber, in the housing, defining a void for receiving the blood from the inlet, the optical chamber comprising at least one optical window for spectroscopic analysis of the blood and an optical chamber depth extending parallel to the depth dimension from the at least one optical window parallel to the depth dimension, wherein an optical chamber width parallel to the width dimension is greater than the optical chamber depth; and an outlet vent, in the housing and fluidly connected to the optical chamber, to provide an outflow path for air; and wherein the inlet transition chamber comprises a tapered transition region bordering the optical chamber, wherein within the tapered transition region the inlet transition chamber width, parallel to the width dimension, increases toward the optical chamber and the inlet transition chamber depth, parallel to the depth dimension, diminishes toward the optical chamber; and an adaptor, wherein the adaptor is fluidly connected to the inlet to receive the blood from a source.

5. The sample holder of claim 2, wherein the optical chamber defines a void, and wherein an optical chamber width parallel to the width dimension is greater than the optical chamber depth.

6. The sample holder assembly of claim 4, wherein the adaptor comprises an adaptor outlet for mating with the inlet in the housing, and an adaptor inlet for receiving the blood from the source, wherein the adaptor inlet is fluidly connected to the optical chamber.

7. The sample holder assembly of claim 6, wherein the adaptor inlet and the adaptor outlet are defined by the ends of a piece of capillary tube.

8. The sample holder assembly of claim 6, wherein the adaptor inlet is configured to accept a syringe.

* * * * *

UNITED STATES PATENT AND TRADEMARK OFFICE
CERTIFICATE OF CORRECTION

PATENT NO. : 7,740,804 B2  Page 1 of 1
APPLICATION NO. : 12/016315
DATED : June 22, 2010
INVENTOR(S) : James Samsoondar It is certified that error appears in the above-identified patent and that said Letters Patent is hereby corrected as shown below:

Title page, item [63]

Continuation of application No. 11/103,619, filed on Apr. 12, 2005, now abandoned.

Should read:

Continuation in part of application No. 11/103,619, filed on Apr. 12, 2005, now abandoned.

Signed and Sealed this

Third Day of August, 2010

David J. Kappos
*Director of the United States Patent and Trademark Office*